United States Patent [19]
Teramachi

[11] Patent Number: 5,496,730
[45] Date of Patent: Mar. 5, 1996

[54] ORGANIC WASTE RECYCLING APPARATUS

[75] Inventor: Kazuo Teramachi, Nagoya, Japan

[73] Assignee: Kabushiki Kaisha Toyodynam, Nagoya, Japan

[21] Appl. No.: 230,398

[22] Filed: Apr. 20, 1994

[30] Foreign Application Priority Data

Dec. 1, 1993 [JP] Japan .................. 5-338830

[51] Int. Cl.$^6$ .............................. C12M 1/06; C12M 1/02
[52] U.S. Cl. ........................ 435/290.2; 435/819
[58] Field of Search ............................. 435/287, 243, 435/312, 313, 315, 316, 813, 819; 422/184; 71/9

[56] References Cited

U.S. PATENT DOCUMENTS

| | | | |
|---|---|---|---|
| 3,923,955 | 12/1975 | Fattinger | 423/210 |
| 4,082,532 | 4/1978 | Imhof | 71/8 |
| 4,135,908 | 1/1979 | Widmer | 71/9 |
| 4,326,874 | 4/1982 | Burklin | 71/9 |
| 4,374,804 | 2/1983 | Easter | 422/184 |
| 5,258,306 | 11/1993 | Goldfarb | 435/316 |

FOREIGN PATENT DOCUMENTS

| | | | |
|---|---|---|---|
| 2856553 | 7/1980 | Germany | 422/184 |
| 4130078 | 5/1992 | Japan | 435/316 |
| 4260682 | 9/1992 | Japan | 435/316 |
| 5254974 | 10/1993 | Japan | 435/316 |

*Primary Examiner*—William H. Beisner
*Attorney, Agent, or Firm*—Flynn, Thiel, Boutell & Tanis

[57] ABSTRACT

A composter including a fermentation compartment located on top of a compost drying compartment. A shutter is located between the compartments to control the transfer of composted material into the drying compartment. In an alternative composter the drying compartment tank is horizontally adjacent the fermentation compartment. A stirring screw is located in the fermenting compartment. During the fermenting process, the stirring screw is rotated back and forth so as to continually mix the material being composted. Once the composting process is completed, the stirring screw is rotated in one direction to transfer the composted material through openings in a separation wall and into the drying compartment.

18 Claims, 8 Drawing Sheets

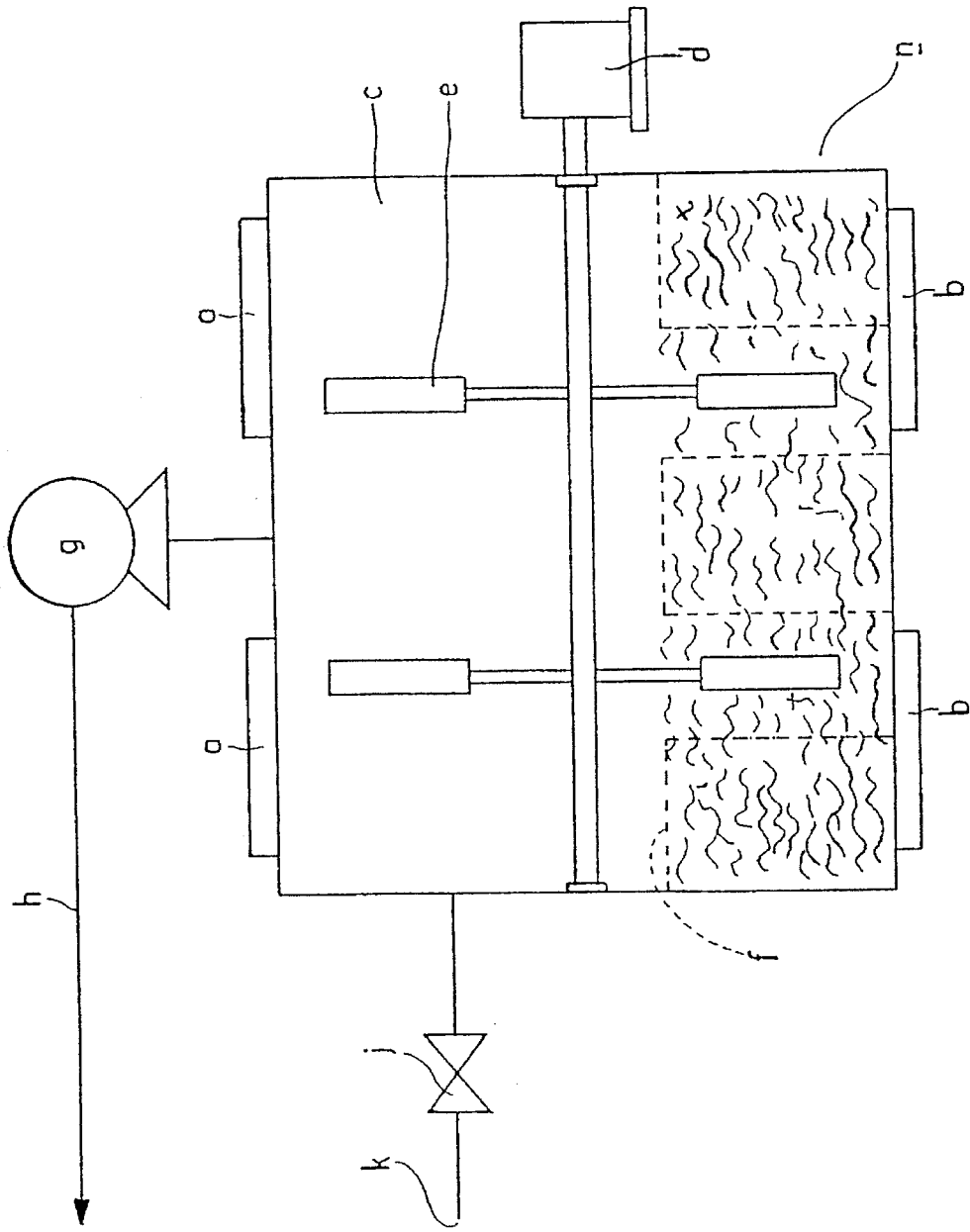

ORGANIC WASTE RECYCLING APPARATUS

BACKGROUND OF THE INVENTION

1. Field of the Invention

The present invention relates to an improved method of recycling organic waste, such as cut grass, garbage and food leftovers, and an improved recycling apparatus.

2. Prior Art

It is known to dry and burn, heap compost, or bury underground organic waste, such as cut grass, garbage scrapped from kitchens, livestock waste, and waste fish parts. With the aforementioned methods, however, there are numerous disadvantages. Burning after drying takes significant amounts of time and labor, and it generates undesirable odors. Composting by heaping up or burying underground takes a long time, causes undesirable odors to develop and also requires a significant amount of land.

A known compositing device n used to treat organic waste, is shown in FIG. 8. The said compositing device n comprises a fermentor c which has the opening a to throw waste and the aperture b to take out treated waste. The rotation of a stirring blade e in the fermentor c is controlled by a motor d. The revering face f is attached around the fermentor c. The exhaust pipe h with the blower g and the air intake k with the valve j are respectively connected to the fermentor c.

With the above-mentioned fermenting device n, organic waste is deposited into the opening a and into the fermentor c. Then, a fermenting aerobe is added. The waste is then composited aerobically the said waste by heating at 40°~60° C. and stirring slowly to make composite. Simultaneously, exhaust gas which is given off compositing process in the fermentor c is drawn through the exhaust pipe h by the blower g. Supply air is provided through the air intake k by opening the valve j. The compost is dried by blowing hot air through the air intake k and heating at 80° C.

Compositing device n has shortcomings. For example, the environmental pollution by stench and low heater efficiency is a problem because gas in the fermentor c is exhausted to the outside through exhaust pipe h. It is difficult to select suitable structure and material for both fermenting and drying process in the fermentor c because each process has respectively different stirring and heating conditions. Moreover, it is necessary to secure vast location because the fermenting device n is located on the ground.

SUMMARY OF THE INVENTION

It is an object of the present invention to provide a method of recycling organic waste and a recycling apparatus to improve the working environment by removing the odoriferous components of gas produced by a fermentor and a drying device, to recycle organic waste with low energy by circulating hot air, to repeatedly use compositing aerobe bacteria during compositing, to execute fermenting and drying treatment smoothly, and to minimize surface needed to perform compositing.

To overcome the above shortcomings, such as low heating efficiency, environmental pollution by stench, difficulty of selecting suitable structure and necessity of vast setting space, the method of recycling organic waste and a recycling apparatus according to the present invention removes odoriferous gas components by connecting an exhaust pipe and a circulatory pipe which has a deodorizing function to a fermentor and a drying device. This holds heat loss to a minimum by the said circulatory pipe, facilitates smooth fermenting and drying and minimizes the air space required by the insertion.

Furthermore, it is possible to ferment organic waste by a fermenting device, pellet composted waste by a manufacturing device, and dry pelleted waste by a drying device to make pelletized compost.

As to the composting device, there are mainly two types. One includes a fermentor which has heating and stirring mechanism. Another includes both a fermentor and a drying device which have respectively heating and stirring mechanism. The fermentor and drying device are connected with an exhaust pipe and a circulatory pipe which have deodrant function.

Since the composting device is composed of both an upper fermentor and a lower drying device which have heating and stirring mechanism, there are mainly two types. That is, one is composed of an upper fermentor and a lower drying device which are connected mutually through an opening at which a shutter is fixed and a projecting dam is arranged. Another is composed of an underground fermentor and an underground drying device. In the said fermentor, a stirring screw turns and reverses freely in horizontal direction. The drying device abuts to the said fermentor in the direction which the said stirring screw advances. Between the fermentor and the drying device, there is a separate wall in which many passage holes are bored.

Moreover, a ventilator, an air intake and a dehumidfier are respectively arranged on the way of a circulatory pipe, while the second deodrant tank containing chlorine dioxide solution is arranged on the way of an exhaust pipe.

The above and other objects, features and advantages of the present invention will become more apparent from the following description when taken in conjunction with the accompanying drawings in which preferred embodiments of the present invention are shown by way of illustrative examples.

BRIEF DESCRIPTION OF THE DRAWINGS

FIG. 8 is a schematic view of a conventional fermenting device.

DESCRIPTION OF THE PREFERRED EMBODIMENT

A method of recycling organic waste and a recycling apparatus according to the present invention will be described with reference to FIG. 1 to FIG. 8.

Figure 1:
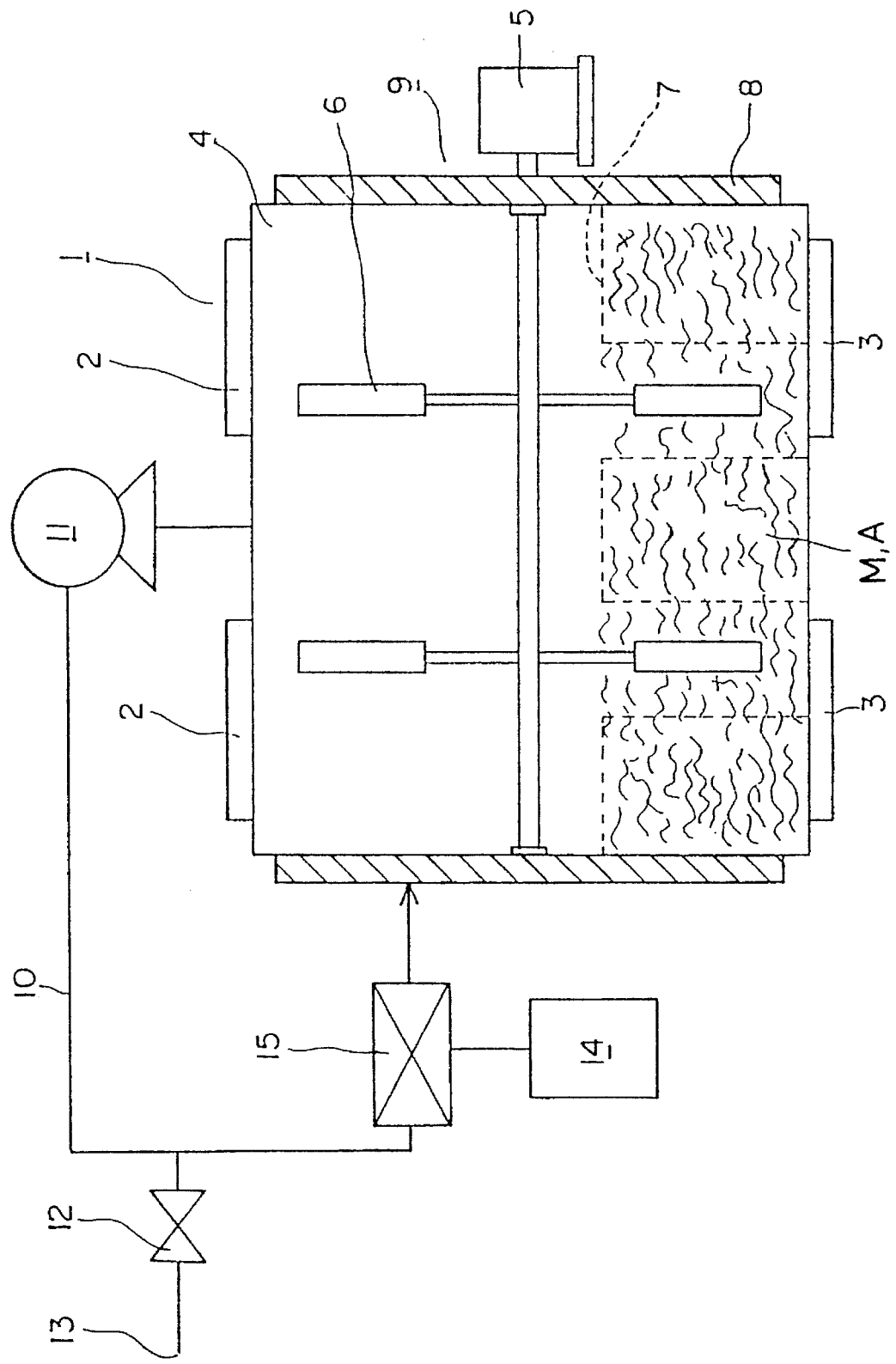
FIG. 1 is a schematic view of a fermenting device according to the present invention.

The reference numeral 1 shown in FIG. 1 represents a composting device to make the pelletized compost C by fermenting the organic waste M. The composting device 1 includes a fermenting tank 4, at the top of which there is a lidded opening 2 to throw waste at the bottom of tank 4 is 9 lidded aperture 3 to take out treated waste. A stirring blade 6 in tank 4 is driven by the motor 5. The motor 5 is fixed to a side of the fermenting tank 4. A fermentor 9 includes an internal heating element 7 and the insulation 8 arround fermenting tank 4.

A circulatory pipe 10 is connected to the fermentor 9. A ventilator 11, an air intake 13 with valve 12, and dehumidifier 15 with dehumidified water collector 14, are coupled to the circulatory pipe 10.

Figure 2:
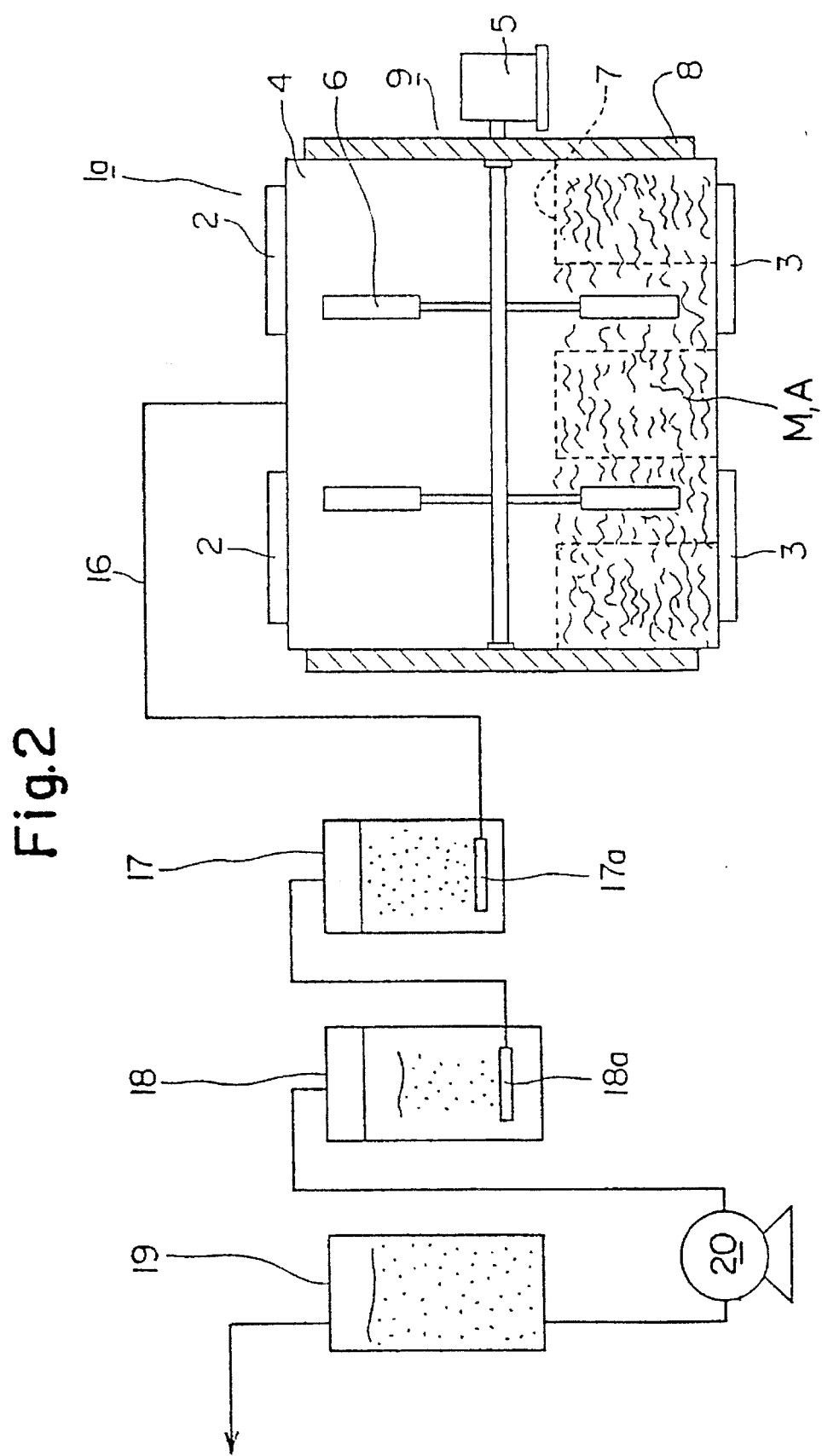
FIG. 2 is a schematic view of other embodiment of a fermenting device shown in FIG. 1.

The fermenting device 1a shown in FIG. 2 has the same basic fermentation tank 9.

The exhaust pipe 16, instead of the circulatory pipe 10, is connected to the fermentor 9. A first deodorizing tank 17 containing water, a second deodorizing tank 18 containing chlorine dioxide solution, and the third deodorizing tank 19 containing activated carbon, are respectively serially coupled to the exhaust pipe 16. A vacuum pump 20 is also coupled to the exhaust pipe 16, to draw gas out of the fermentor 9 through the first deodorant tank 17, the second deodrant tank 18 and the third deodrant tank 19 to the outside.

At each section end of the exhaust pipe 16 in the first deodrant tank 17 and the second deodrant tank 18, the bubble nozzles 17a, 18a are, respectively, equipped. The inlet side of the vacuum pump 20 is connected to the top of the second deodrant tank 18, while the outlet side is connected to the lower opening of the third deodrant tank 19.

The chlorine dioxide solution in the second deodrant tank 18 is made by dissolving chlorine dioxide 10 cc per water 100 cc. It is desirable to stabilize chlorine dioxide in order to prevent chlorine dioxide from being rapidly dissolved.

Moreover, as other embodiment, the compositing device 1b shown in FIG. 3 will be described as follows.

Figure 4:
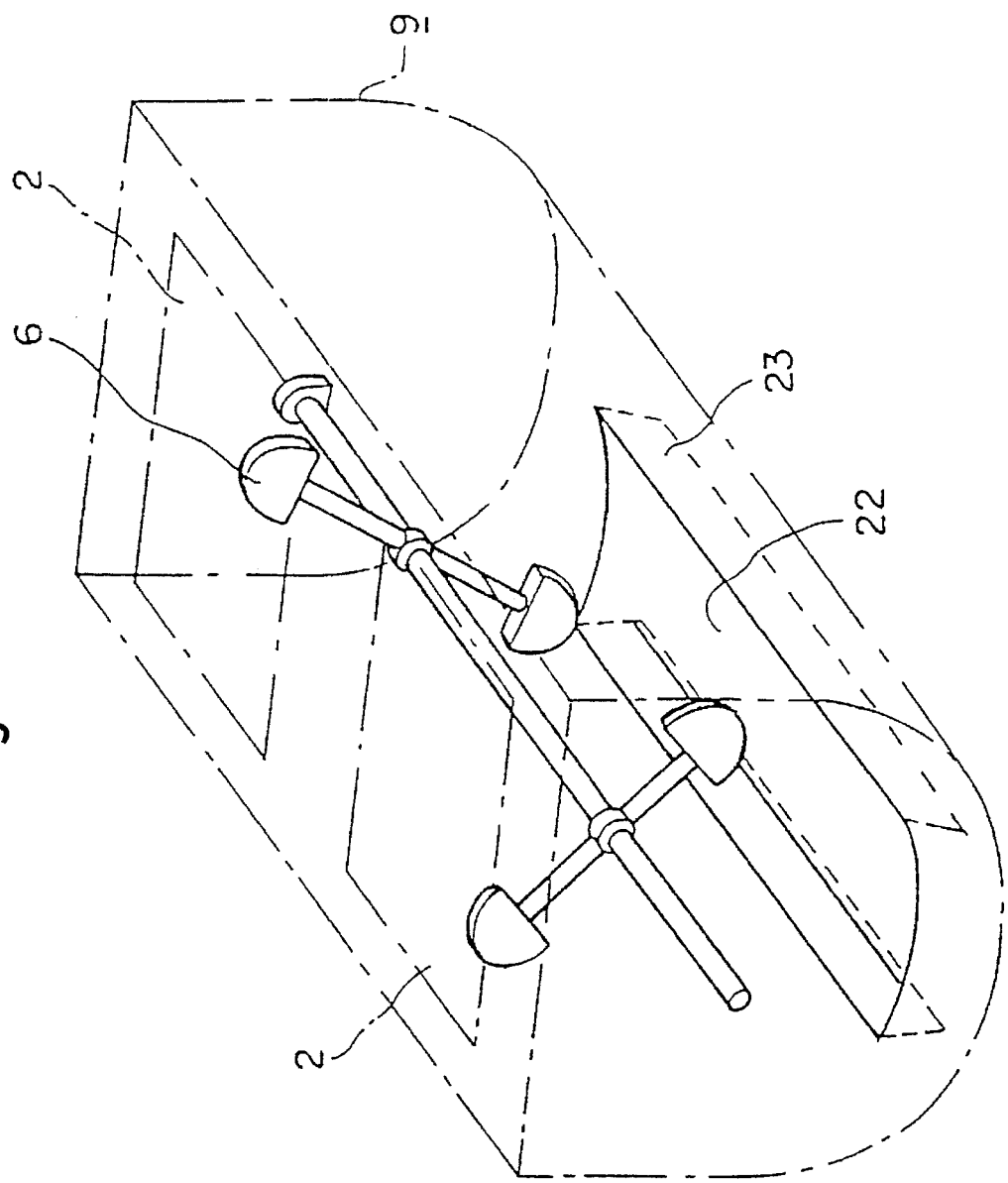
FIG. 4 is a roughly perspective view of a fermentor of fermenting device shown in FIG. 1.
Figure 5:
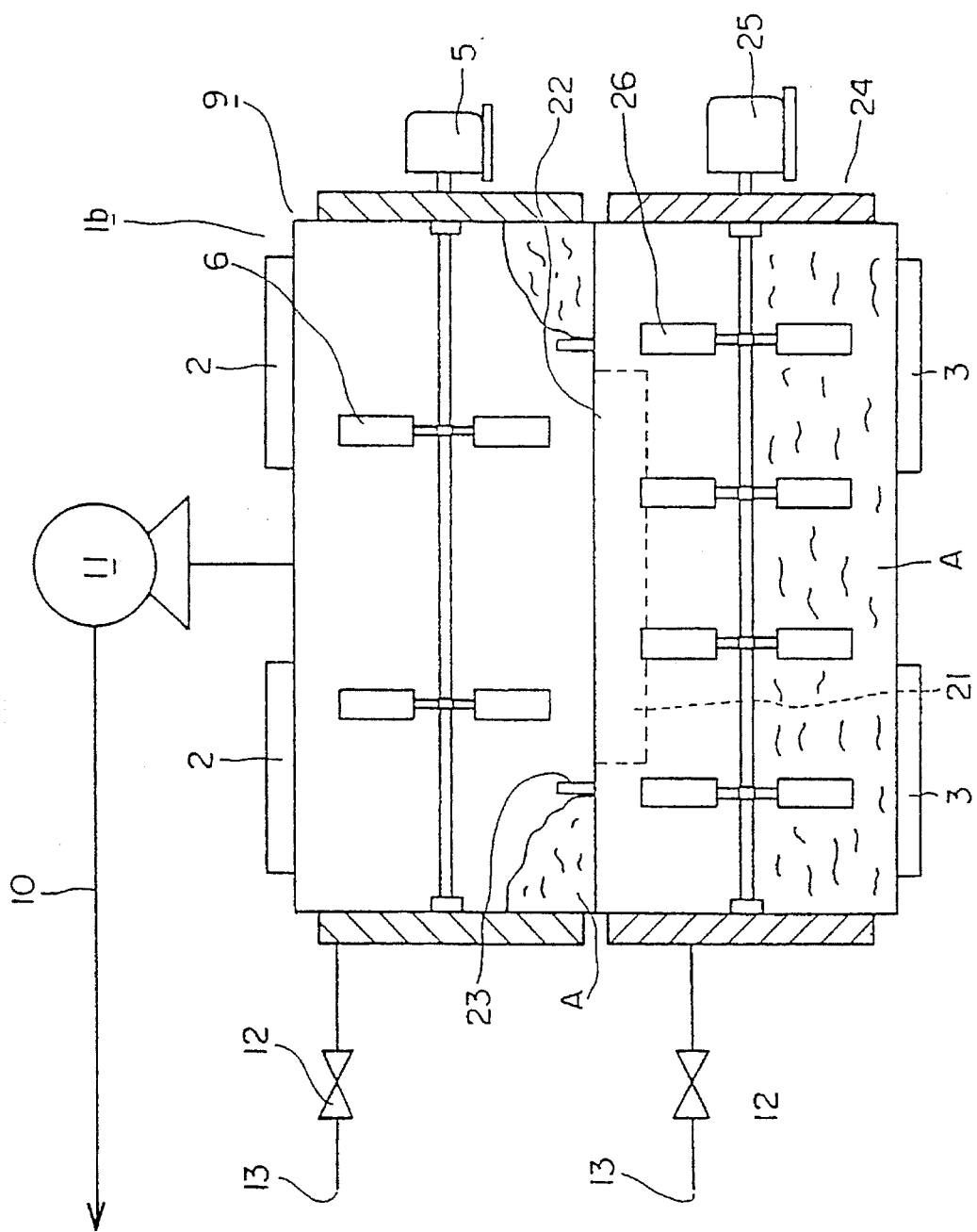
FIG. 5 is a schematic view of a drying device of a fermenting device shown in FIG. 3 wherein fermented waste in a fermentor is fallen through an opening into a drying device.

Instead of the aperture 3 of the fermentor 9, the opening 22 is equipped at the bottom of the fermenting tank 4. The shutter 21 is arranged at the said opening 22, to open and shut freely. An upwardly projecting dam 23 is projectingly fixed at the edge arround the opening 22. With such an arrangement, the fermentor 9 is composed, as shown in FIG. 4.

The said fermentor 9 is seated over the drying tank 24 which opens upward. The fermentor 9 and the drying tank 24 are connected each other through the opening 22.

The stirring blade 26 in the drying tank 24 is driven by the motor 25 which is equipped at the side of the said drying tank 24. The heating plate 7 and the insulation 8 are attached arround the drying tank 24. The lidded aperture 3 is arranged at the bottom of the drying tank 24.

The air intake 13 with the valve 12 is connected to the drying tank 24. With such an arrangement, the drying device is composed.

It is possible that the upper fermentor 9 is connected with the circulatory pipe 10 on the way of which the ventilator 11, the valve 12, the air intake 13, the dehumidified water collector 14 and the dehumidfier 15 of the fermenting device 1 are arranged. It is also possible that the fermentor 9 is connected with the exhaust pipe 16 on the way of which the first deodrant tank 17, the second deodrant tank 18, the third deodrant tank 19 and the vacuum pump 20 of the fermenting device 1a are respectively arranged.

Furthermore, it is possible to connect the circulatory pipe 10 or/and the exhaust pipe 16 to the lower drying device 27.

As other embodiment, the compositing device 1c shown in FIG. 6 will be described as follows.

The fermentor 9 of the fermenting device 1c is located under the ground. The lidded opening 2 is located at ground level GL. The fermenting tank 4 is constructed with the wall 28 which is made of fiberglass, tempered plastic or concrete. A aboveground motor 5 is attached to the fermenting tank 4. A stirring screw 31 in the fermenting tank 4 is driven by the motor 5 through the pullies 29, 29a and the belt 30.

The hollow rotary shaft 32 of the stirring screw 31 is connected to the aboveground hot air blowing 34. Jets 33, 33a . . . are formed along the rotary shaft 32 of stirring screw 31.

The underground drying device 27 is located at position at which waste is sent by the stirring screw 31 in the fermentor 9. A lidded aperture 3 is located at ground level GL. The said drying device 27 is constructed with wall 28 which is made of fiberglass tempered plastic or concrete.

Between the fermentor 9 and the drying device 27, there is the separating wall 35 at which the passage holes 36 are bored. A screw conveyer 37 is positioned under the aperture 3 in the drying device 27.

It is possible that the fermentor 9 is connected with the circulatory pipe 10 on the way of which the ventilator 11, the valve 12, the air intake 13, the dehumidified water collector 14 and the dehumidfier 15 of the compositing device 1 are respectively arranged. It is also possible that the fermentor 9 is connected with the exhaust pipe 16 on the way of which the first deodorizing tank 17, the second deodorizing tank 18, the third deodorizing tank 19 and the vacuum pump 20 of the compositing device 1b are respectively arranged.

It is possible to connect the circulatory pipe 10 or/and the exhaust pipe 16 to the lower drying device 27.

Figure 7:
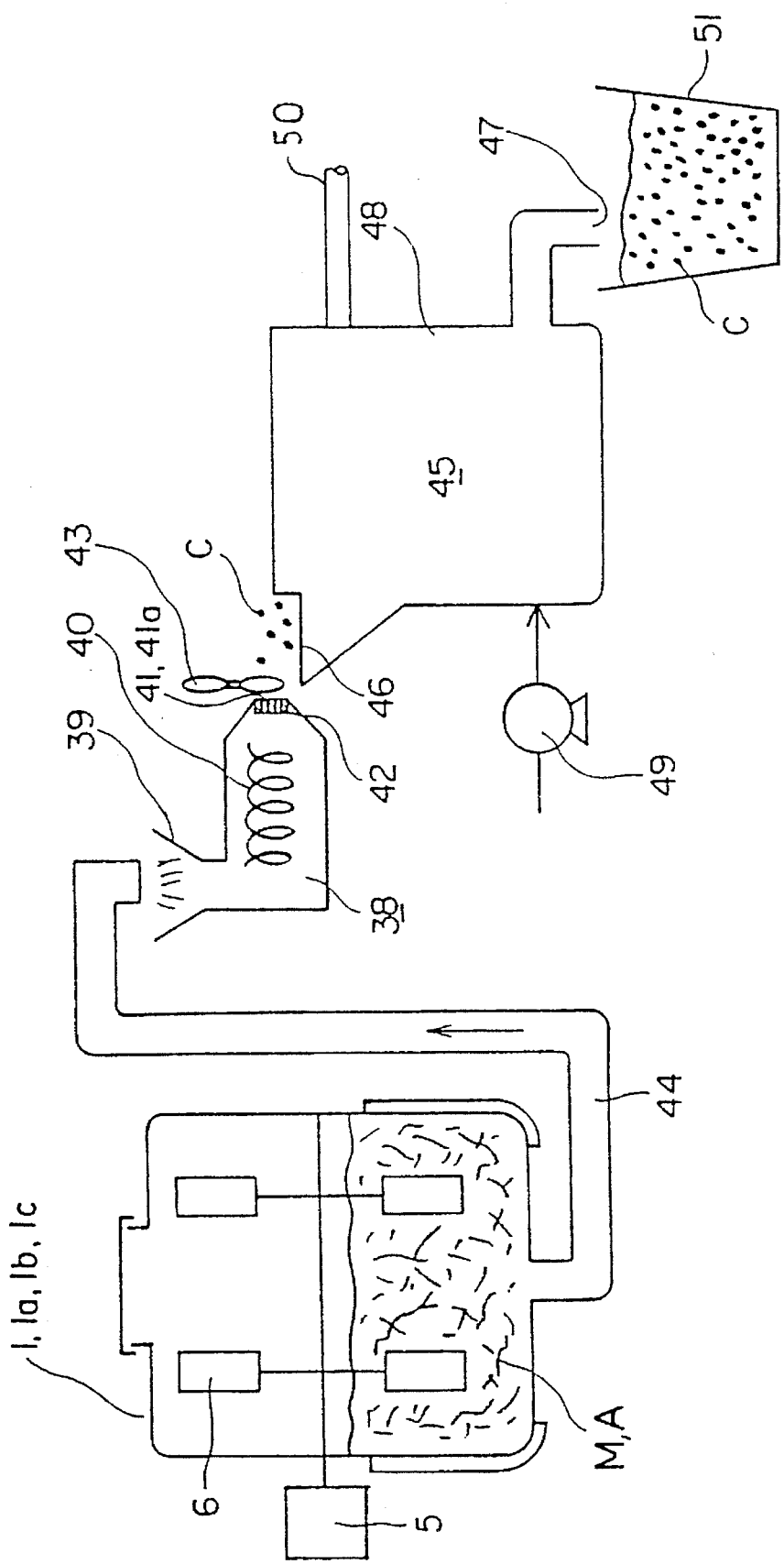
FIG. 7 is a schematic view of a recycling apparatus according to the present invention which comprises a fermenting device, a manufacturing device for pellet and a drying device for pellet.

As shown in FIG. 7, the manufacturing device for pellet 38 includes a screw press 40 at which the hopper 39 is equipped. The composted waste A, which is treated by the compositing devices 1, 1a . . . , is transferred into the hopper 39. The exhaust holes 41, 41a . . . are bored at the exhaust plate 42 which is attached to the exhaust tip of the screw press 40. The treated waste is pressed out of the exhaust holes 41, 41a . . . of the exhaust plate 42. A cutter 43, which is located adjacent the back of the exhaust plate 42, cuts the pressed columnar one at a regular length.

The reference numeral 44 shown in FIG. 7 represents a transfer pipe for the composted waste. The transfer pipe 44 is arranged between the compositing devices 1, 1a . . . and the pelletizer 38.

The pellet drying apparatus for 45 includes container 48 which has the opening 46 through which the pellet are fed and the aperture 47 through which the pellets are discharged. The pelletized compost C which is made by the manufacturing device 38, is discharged directly into a hot air blower 49 and exhaust pipe 50 are respectively connected to the container 48.

It is possible to connect the circulatory pipe 10 or/and the exhaust pipe 16 to the manufacturing device 38 and the drying apparatus 45 in order to remove undesirable odors.

A method of recycling organic waste according to the present invention will be described hereafter.

The method of this invention includes the steps of throwing the organic waste M and fermenting aerobe through the opening 2 into the fermentor 9 of the compositing devices 1, 1a, 1b or 1c. Stirring blade 6 or the stirring screw 31 is actuated by the motor 5. The organic waste M is heated to approximately 40°–60° C. for 24 hours by the heating element 7 and the ventilator of hot wind 34 in order to make the composted waste A. The organic waste M comprises mown grass, garbage, excrement or fish waste.

It is possible to draw odoriferous gas out of the fermentor 9 of the compositing devices 1, 1a . . . into the circulatory 10. Water, which is contained in the said odoriferous gas, is condensed with odor causing contaminants by the dehumidifier 15. The collected water in the dehumidified water collector 14 is disposaled after deodorizing treatment.

In the abeve-mentioned condition, it is necessary for compositing to take enough air through the air intake 13 by opening the valve 12.

As shown in FIG. 2, by the vacuum pump 20, gas the fermentor 9 is drawn into the exhaust pipe 16 of the compositing devices 1, 1a . . . . The said gas is jetted into the water in the first deodorizing tank 17 through the bubble nozzle 17a and aerated so that water-soluble odor causing ingredients such as ammonia are removed. Simply then the gas containing other ingredients is jetted into chlorine dioxide solution in the second deodorizing tank 18 through the buble nozzle 18a and aerated so that other odor-causing ingredients are oxidized and resolved. The gas containing the remaining odor-causing ingredients is fed into the third deodorizing tank 19 so that almost all of the remaining odor-causing ingredients are filtered out by activated carbon.

As shown in FIG. 7, the composted waste A, which is made by the composted devices 1, 1a . . . , is discharged into the hopper 39 (if necessary, with water and binder). The composted waste A is mixed and kneaded by the screw press 40, and then pressed as a cords out of the exhaust holes 41, 41a . . . of the exhaust plate 42. The cutter 43 cuts the pressed waste A to make the pelletized compost C.

As to the size of the pelletized compost C, the diameter is 2~5 mm, and the length is 3~7 mm.

The pelletized compost C is discharged through the opening 46 into the drying apparatus for pellet 45, dried at 50°~60° C. by hot air from the ventilator 49, and taken out to the vessel 51. The treated pelletized compost C is scattered as a manure for grass in golf courses, crops in farm, and plants.

Figure 3:
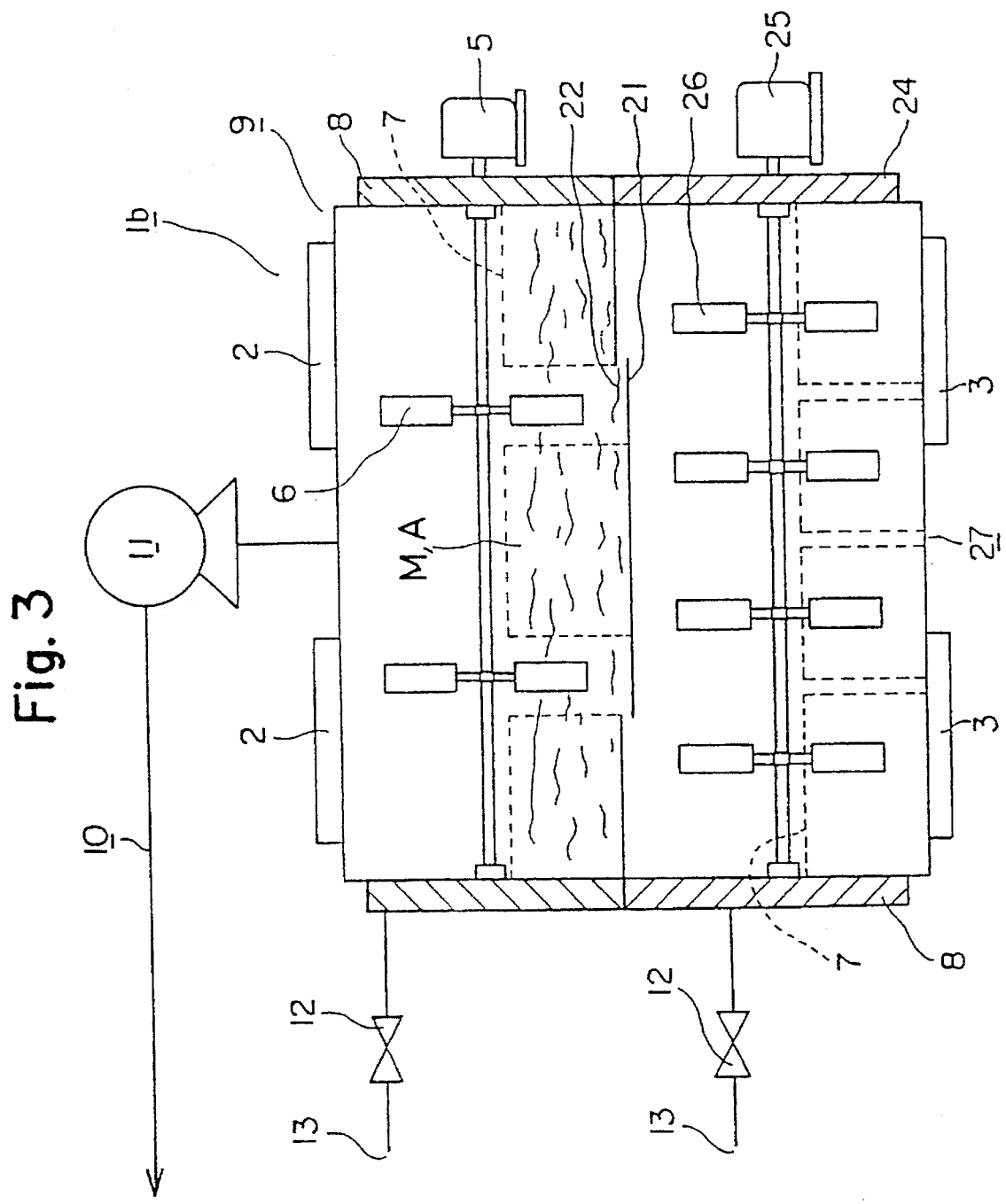
FIG. 3 is a schematic view of other embodiment of a fermenting device shown in FIG. 1.

As shown in FIG. 3, the manner of operation of the compositing device 1b will be described hereinafter.

The compost device 1b composts waste in the fermentor 9 to make the composted waste A. The shutter 21 opens downward on both sides, the composted waste A falls through the opening 22 into the drying device 27.

At that time, a portion of the composted waste A is remained in the fermentor 9 because the projecting dam 23 is fixed at the opening 22 as shown in FIG. 4. However, the remained compost waste A can be used as a stock for the next composting process.

Furthermore, the motor 25 drives the stirring blade 26 to stir the fermented waste A in the drying device 27, at the same time, the heating element 7 heats and drys composted waste.

In the above-mentioned process, the composted waste A is heated and dried at 70°~80° C., by opening the valve 12 and taking hot wind through the air intake 13.

The explanation of deodorizing in fermenting and drying process will be omitted because it is the same with the above-mentioned. And manufacturing process of the pellet manure C will be also omitted.

As to the composting device 1b, it is possible to excute both composting and drying process at the same time, which makes it possible to utilize the same heat for both processes.

Figure 6:
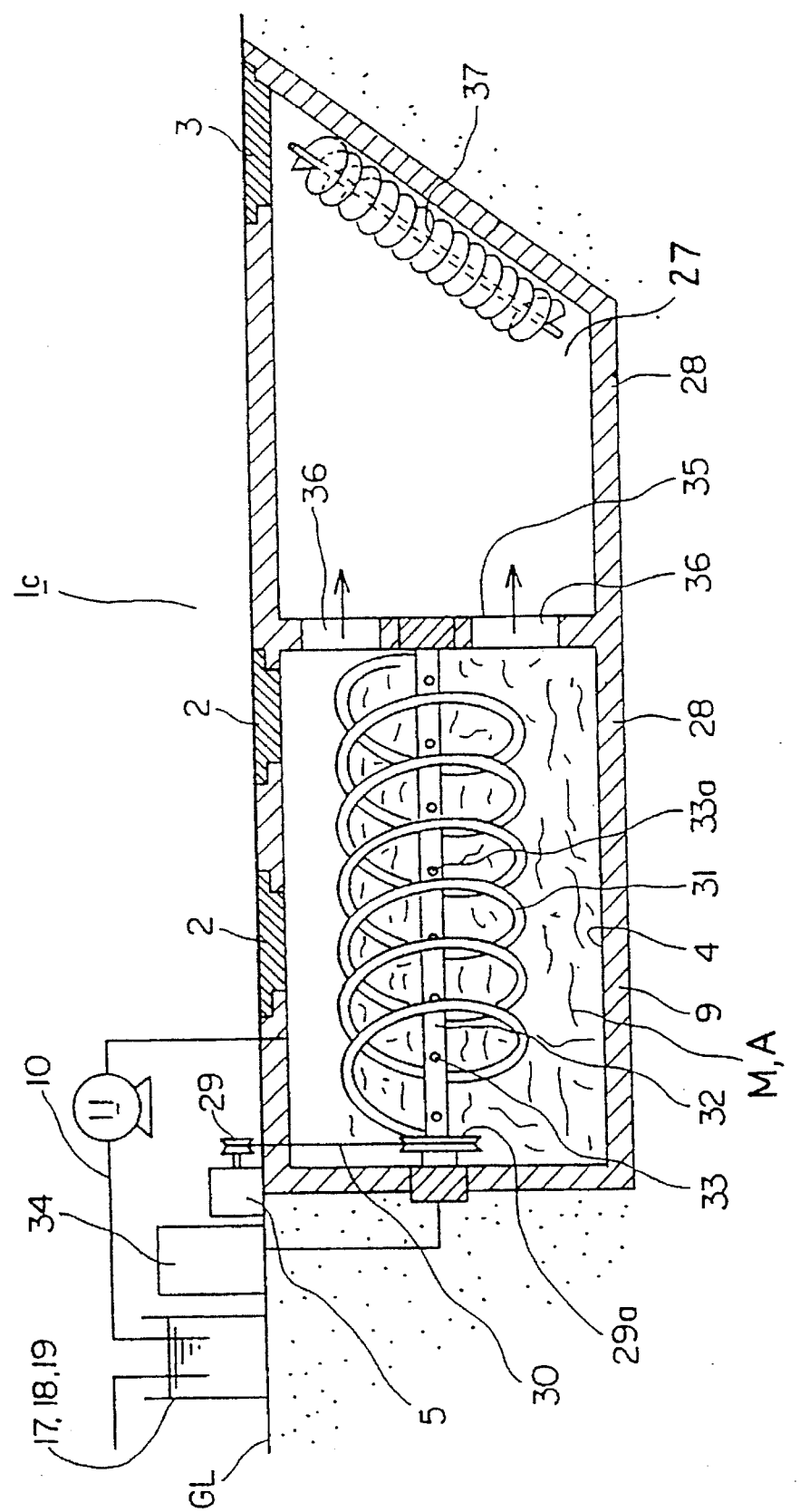
FIG. 6 is a schematic view of other embodiment of a fermenting device shown in FIG. 1.

As shown in FIG. 6, when the organic waste M with fermenting aerobe is thrown into the fermentor 9, the motor 5 turns and inverts the stirring screw 31 to stir the organic waste M. Then, hot wind, is sent through the jets 33, 33a . . . of the hollow rotary shaft 32 by the ventilator 34, heats and ferments the organic waste M.

In this composting process, the composted waste A doesn't intrude into the drying device 27 because the A is pushed back and forth along the shaft 32 by the forward and reverse movements of the screw 31.

The motor 5 then drives the stirring screw 31 in one direction so that the composted waste A is transfered through the passage holes 36 of the separate wall 35 into the drying device 27. The composted waste A is dried spontaneously, or heated and dried at under 80° C. with hot air. Then, the composted waste A is removed through the opening 3 by the screw conveyer 37.

The explanation of deodorizing fermenting and drying processes and the manufacturing process for pellets will be omitted because it is the same with the above-mentioned embodiments of the invention.

As mentioned above, a recycling apparatus according to the present invention comprises the composting device 1 which is composed by connecting the ventilator 11, the air intake 13 and the dehumidfier 15 to the fermentor 9. The fermentor 9 has a heating and stirring mechanism. A method of recycling organic waste according to the present invention comprises a way of composting and deodorizing the organic waste M by the composting device 1. The odoriferous gas, which is given out in the composting process, is fed into the dehumidifier 15 by the ventilator 11. Heated air is recirculated back into the fermentor 9 without being exhausted to the outside environment. Water containing odor-causing ingredients is dehumidifed. As a result, this closed-system saves energy by decreasing the loss of thermo energy and improves the working environment by deodorizing the air used in the process.

Furthermore, it is possible to manufacture compost for a short time without stench because the pelletized compost C is made by pelletizing and drying the composted waste A. This invention eliminates the need to devote large areas to the drying, burning heap composting or burying of waste. On a golf course, a recycling apparatus can be employed to recycle waste composed of cut grass into compost.

Moreover, as to the composting device 1b, the upper fermentor 9 and the lower drying device 27 have respectively heating and stirring mechanism. Composted waste transferred to the drying device 27 by shutter 21. At fermenting the organic waste M by the opening the shutter 21 downward to both sides. A portion of the composted waste A remains adjacent at the projecting dam 23 around the opening 22 of the fermentor 9. As a result, it is possible to recycle the remaining composted waste A during the next fermenting process.

Furthermore, the second deodorizing tank 18 which contains chlorine dioxide solution is arranged on the way of the exhaust pipe 16 of the fermentor 9 which has heating and stirring mechanism so that odor-causing ingredients of gas which are given off during composting are removed. As a result, it is possible have a working environment that is clean and comfortable.

Moreover, the composting device 1c includes the underground fermentor 9 and the underground drying device 27. In the fermenting tank 4 of the said fermentor 9, there is the stirring screw 31 which freely rotates forward and reverse directions. The drying device 27 is adjoined to the said fermentor 9 at the location at which waste is sent by the stirring screw 31. Between the fermentor 9 and the drying device 27, there is the separate wall 35 at which the passage holes 36 are bored. In fermenting process, the motor 5 drives the stirring screw 31 back and forth. The composted waste A is stirred, advancing and retreating in the shaft direction of the rotary shaft 32 so that it is fermented without entering into the drying device 27, thoroughly composted waste A is transferred through the passage holes 36 of the separate wall 35 into the drying device 27 by rotating the stirring screw 31 by the motor 5 in one direction so as to cause forward movement of the waste. As a result, it is possible to perform composting and drying treatment smoothly. It is also possible to set the fermentor 9 and the drying device 27 under the ground so that there is no need to provide large amounts of surface area for the composter.

Although the invention has been described in its preferred form with a certain degree of particularity, it is to be understood that the present invention is not limited in practical application to the specific embodiments described herein. Changes and variations are possible to the invention without departing from the scope and spirit of what is claimed below.

What is claimed is:

1. A composter comprising:
   a composter housing having an inner wall, said composter housing further having an upper section that defines a fermentation compartment and a lower section that defines a drying compartment;
   a partition panel extending inwardly from said composter housing inner wall so as to define said composter housing into said upper and lower sections, said partition panel being formed with a through passage between said sections that is spaced inwardly from said composter housing inner wall, said partition panel including an upwardly extending lip that extends around said through passage;
   a shutter seated in said partition panel through passage for selectively opening and closing said through passage;
   a first set of stirring blades disposed in said fermentation compartment;
   a second set of stirring blades disposed in said drying compartment;
   a first set of heating elements disposed in said drying compartment for heating said drying compartment to a first temperature; and
   a second set of heating elements disposed at said fermentation compartment for heating said fermentation compartment to a second temperature, said second selected temperature being less than said first temperature to which said drying compartment is heated.

2. The composter of claim 1, further including a hot air blower assembly connected to said composter housing lower section for supplying heated air to said drying compartment.

3. The composter of claim 1, further including an exhaust system connected to said composter housing upper section for withdrawing gas from said fermentation compartment, said exhaust system having a pipe coupled to said composter housing lower section for directing the exhausted gas from said fermentation compartment to said drying compartment.

4. The composter of claim 3, wherein said exhaust system includes a filtration system for removing contaminants from the gas withdrawn from said fermentation compartment.

5. The composter of claim 3, wherein said first and second sets of said heating elements are configured to heat said fermentation compartment to a temperature 10° to 40° C. lower than said temperature of said drying compartment.

6. The composter of claim 1, wherein said partition panel has a downwardly curved concave profile and said through passage is located in a lower portion of said partition panel.

7. The composter of claim 6, wherein said first and second sets of said heating elements are configured to heat said fermentation compartment to a temperature 10° to 40° C. lower than said temperature of said drying compartment.

8. The composter of claim 1, wherein said first set of heating elements are configured to heat said drying compartment to a temperature between 70° to 80° C.

9. The composter of claim 8, wherein said second set of heating elements are configured to heat said fermentation compartment to a temperature between 40° to 60° C.

10. The composter of claim 1, wherein said second set of heating elements are configured to heat said fermentation compartment to a temperature between 40° to 60° C.

11. A composter comprising:
    a composter housing having an interior space, said composter housing including a vertically extending dividing wall for dividing said composter housing interior space into a fermentation compartment and a drying compartment, said dividing wall being formed with an opening to facilitate the transfer of compost from said fermentation compartment to said drying compartment;
    a horizontally aligned stirring screw disposed in said fermentation compartment and extending the length thereof, said stirring screw being shaped to horizontally move material being composted so that when said screw rotates in a first direction, said material is displaced toward said dividing wall and when said screw rotates in a second direction opposite said first direction, said material is displaced away from said dividing wall; and
    a motor attached to said stirring screw for rotating said screw in said first and second directions, said motor being configured to have a first mode of operation during which said motor alternatively rotates said stirring screw in said first and second directions and a second mode of operation in which said motor continually rotates said stirring screw in said first direction.

12. The composter of claim 11, further including a discharge opening formed in said composter housing adjacent said drying compartment and further including a transfer screw disclosed in said drying compartment for moving composted material towards said discharge opening.

13. The composter of claim 11, wherein said composter housing has a base surface and said dividing wall opening is located in said dividing wall above said composter housing base surface.

14. The composter of claim 11, further including a hot air ventilator coupled to said composter housing for providing heated air to said fermentation compartment.

15. The composter of claim 14, wherein said stirring screw is provided with a hollow shaft, said shaft being formed with a plurality of openings and said hot air ventilator is coupled to said stirring screw shaft so as to introduce air into said fermentation compartment through said stirring screw shaft openings.

16. The composter of claim 11, wherein said stirring screw is rotatably secured to said dividing wall.

17. The composter of claim 16, wherein said composter housing has a base surface and said dividing wall is formed with said opening located between said composter housing base surface and the location on said dividing wall at which said stirring screw is secured to said wall and is further formed with a second opening located above the location on said dividing wall at which said stirring screw is secured to said wall.

18. The composter of claim 16, wherein: a hot air ventilator is coupled to said composter housing for providing heated air to said fermentation compartment; and said stirring screw is provided with a hollow shaft, said shaft being formed with a plurality of openings and said hot air ventilator is coupled to said stirring screw shaft so as to introduce air into said fermentation compartment through said stirring screw shaft openings.

* * * * *